(12) United States Patent
Ritter et al.

(10) Patent No.: US 9,440,015 B2
(45) Date of Patent: Sep. 13, 2016

(54) BLOOD PURIFICATION MACHINE COMPRISING HEATED FLUID CIRCUIT

(71) Applicant: B. BRAUN AVITUM AG, Melsungen (DE)

(72) Inventors: Kai-Uwe Ritter, Melsungen (DE); Thore Heinemann, Soehrewald (DE); Guenter Niemetz, Melsungen (DE)

(73) Assignee: B. BRAUN AVITUM AG, Melsungen (DE)

( * ) Notice: Subject to any disclaimer, the term of this patent is extended or adjusted under 35 U.S.C. 154(b) by 346 days.

(21) Appl. No.: 14/135,820

(22) Filed: Dec. 20, 2013

(65) Prior Publication Data

US 2014/0174698 A1 Jun. 26, 2014

(30) Foreign Application Priority Data

Dec. 24, 2012 (DE) .................. 10 2012 113 086

(51) Int. Cl.
| | |
|---|---|
| B01D 21/30 | (2006.01) |
| A61M 1/16 | (2006.01) |
| C02F 9/00 | (2006.01) |
| A61L 2/18 | (2006.01) |

(52) U.S. Cl.
CPC .............. *A61M 1/1686* (2013.01); *A61L 2/18* (2013.01); *A61M 1/1662* (2014.02); *A61M 1/1688* (2014.02); *A61M 2205/366* (2013.01)

(58) Field of Classification Search
None
See application file for complete search history.

(56) References Cited

U.S. PATENT DOCUMENTS

| | | | |
|---|---|---|---|
| 3,228,465 A | 1/1966 | Vadot | |
| 3,738,382 A | 6/1973 | Cappelea, Jr. et al. | |
| 3,744,636 A | 7/1973 | Commarmot | |
| 4,055,496 A * | 10/1977 | Friedrich | A61M 1/16 210/195.2 |
| 4,982,782 A * | 1/1991 | Albers | B01D 1/14 165/111 |
| 5,147,613 A | 9/1992 | Heilmann et al. | |
| 5,647,984 A | 7/1997 | Hovland et al. | |
| 5,948,247 A | 9/1999 | Gillerfalk et al. | |
| 6,537,450 B2 | 3/2003 | Russell et al. | |
| 2007/0187073 A1 * | 8/2007 | Ikegami | B01D 53/265 165/133 |

FOREIGN PATENT DOCUMENTS

| | | |
|---|---|---|
| DE | 39 36 785 | 3/1991 |
| DE | 696 29 467 | 12/1996 |
| FR | 2 120 507 | 8/1972 |
| JP | S64-64664 | 3/1989 |
| WO | WO 93/09821 | 5/1993 |
| WO | WO 96/40314 | 12/1996 |

OTHER PUBLICATIONS

German Search Report for DE 10 2012 113 086.8 dated Sep. 23, 2013.
European Search Report for EP 13 19 8664 dated Apr. 10, 2014.

* cited by examiner

*Primary Examiner* — Nam Nguyen
*Assistant Examiner* — Richard Gurtowski
(74) *Attorney, Agent, or Firm* — RatnerPrestia

(57) ABSTRACT

A machine for extracorporeal blood treatment comprising a machine-side fluid circuit is disclosed. The machine comprises a heat exchanger for heating cold purification fluid freshly supplied on its intake side, for which purpose used still warm purification fluid flows past its opposite discharge side for a heat exchange, and a circulation valve for changing over between a blood purification mode in which the used purification fluid is disposed of in an open fluid circuit through the discharge side of the heat exchanger into a drain and a disinfection mode in which hot disinfectant is circulated in a closed circuit. The circulation valve is connected downstream of the heat exchanger with respect to the discharge side thereof.

13 Claims, 3 Drawing Sheets

BLOOD PURIFICATION MACHINE COMPRISING HEATED FLUID CIRCUIT

CROSS REFERENCE TO RELATED APPLICATIONS

This application claims priority to German Patent Application No. DE 10 2012 113 086.8 filed Dec. 24, 2012, the contents of such application being incorporated by reference herein.

FIELD OF THE INVENTION

The present invention relates to a blood purification machine comprising an internal fluid circulation adapted to be heated by a heating means.

BACKGROUND OF THE INVENTION

As a rule, blood purification machines serve for use of an extracorporeal blood purification replacement treatment (for example dialysis) especially in the case of renal failure. Apart from renal transplantation, such blood purification replacement treatment or dialysis is the most important renal replacement therapy in the case of chronic renal failure and one of the possible treatments in the case of acute renal failure.

By the term "dialysis" an exchange of substance via a membrane arranged in a dialyser is understood, wherein on one side of the membrane blood/plasma is present and on the other side of the membrane the purifying fluid or else dialysis fluid is present. Concretely speaking, blood is guided out of a patient in an extracorporeal blood circulation to the dialyser of the machine and there is passed by the membrane. On the machine-side, preferably water suited for dialysis is withdrawn from a reservoir or an external line, is processed to form a dialysis fluid in an internal fluid circulation and the fresh dialysis fluid is equally passed to the dialyser so as to absorb contaminants from the blood flowing past.

In so called hemodialysis the principle of adjusting the concentration of small-molecular substances of two fluids is applied which are separated by a semipermeable membrane in the dialyser (osmosis). In this case, separated by the filter membrane, on the one membrane side the blood discharged from the patient's body including nephrotoxins, electrolytes (especially potassium and phosphate) as well as substances usually eliminated with the urine is provided. On the other membrane side the low-germ possibly processed dialysis solution (dialysis fluid) is provided, wherein the water thereof was processed, in case of need, for instance during online processing by reverse osmosis or other known measures, which is initially free of waste products and which includes a content of electrolytes oriented at the particular needs of the patient.

The semipermeable filter membrane (dialyser membrane) between the blood and the dialysis fluid necessarily has pores that allow small molecules such as water, electrolytes and substances usually eliminated with the urine (e.g. urea, uric acid) to pass but withhold large molecules such as proteins and blood cells.

Before the dialysis fluid or purifying fluid in the dialyser flows past the patient's blood, it has to be heated from the original entering temperature of typically approx. 10° C. to a higher temperature, approximately equal to the blood temperature (about 37° C.) so as to avoid cooling of the patient. After the dialysis fluid has flown through the dialyser so as to absorb contaminants from the blood, it is deemed to be used and is discharged in a drain for later disposal.

STATE OF THE ART

It is known from the state of the art to make use of a heat exchanger for exploiting and, resp., partly recovering the thermal energy of the used dialysis fluid for pre-heating fresh (cold) purifying fluid or water suited for dialysis and thus reducing the power consumption of the dialysis machine caused by heating the dialysis fluid or the water suited for dialysis. In this case the (still cold) dialysis fluid or the water is pre-heated, before/upon entry into the fluid circulation, via the heat exchanger by the used and discharged dialysis fluid.

In FIG. 1 an (internal) fluid circulation of a blood purification machine (dialysis machine) is schematically represented as it is also known from the state of the art.

Accordingly, the fluid circulation basically constitutes two switchable circulations, i.e. a purifying or operating circulation and a disinfection circulation, and/or the fluid circulation can be operated in two functioning modes, viz. the blood purification mode (operating mode) and the disinfection mode.

Concretely speaking, the fluid circulation according to the state of the art is connected via a feed line including an intake valve arranged therein to a so called osmosis ring line or simply a water supply line from which fluid losses can be selectively compensated during blood purification treatment. The feed line of the water suited for dialysis first leads into a heat exchanger and from there passes in a pre-heated state (approx. 25° C.) into a first tank of a water processing unit. From there the pre-heated and degasified water is pumped via a suction pump into a preferably electrically operated heating means in which the water is heated to a temperature of approx. 37° C. so as to be passed on into a second tank of the water processing unit which is integrated in the purification or operating circulation.

As can be inferred from FIG. 1, a first conveying line passes the water heated and now treated to form a purifying fluid to a dialyser in which the fluid flows past a membrane separating the purifying fluid from the patient's blood. After the purifying fluid has been contaminated with substances to be removed from the patient's blood, the used fluid is passed into the heat exchanger via a second conveying line connected to the dialyser and including a flow pump connected therein and a stop valve or discharge valve connected thereto so that it is capable of transferring the heat stored in the dialysis fluid (still at about 35° C.) to the newly fed water in order to pre-heat the latter. Subsequently the largely cooled dialysis fluid is disposed of through a drain connected to the heat exchanger.

As indicated already in the foregoing, the dialysis fluid introduced to the dialyser is intended to be as poor in germs as possible. For this purpose, a disinfectant line branch from which optionally a disinfectant can be introduced into the first conveying line via a disinfection pump is connected to the first conveying line.

In accordance with FIG. 1, a dialyser bypass is provided for selectively short-circuiting the first and second conveying lines, for which purpose a stop valve or bypass valve for selectively opening and closing the bypass is arranged in the bypass. Moreover, between the flow pump and the discharge valve a circulation line branch is connected in which a stop valve or circulation valve to be selectively opened/closed is arranged and which opens into the second tank of the water processing unit.

In the typical dialysis operating mode the circulation valve and the bypass valve are closed, whereas the discharge valve and the intake valve are opened. The suction pump and the flow pump are being operated, whereas the disinfection pump is switched off and at the same time prevents purifying fluid from flowing into the disinfection line. At this operating position, the purifying fluid is heated to the operating temperature in an open circuit via the heat exchanger and the successive heating means and is then pumped through the dialyser. The used dialysis fluid is returned to the heat exchanger so as to pre-heat the fresh non-used dialysis fluid there and after that is disposed of via the drain.

According to the state of the art, inter alia hot disinfection, as it is called, is used to disinfect the fluid circulation. For this purpose, a water-disinfectant mixture is heated in the fluid circulation to >85° C. and is circulated there for a predetermined period of time.

Concretely speaking, for this the intake valve and the discharge valve are closed, whereas the bypass valve and the circulation valve are opened. Furthermore, the suction pump is switched off and instead the disinfection pump is put into operation. At this operating position, the disinfectant is circulated through the first and second conveying lines via the bypass as well as via the circulation line and the second tank back into the first conveying line.

As can be inferred from the foregoing description, the heat exchanger is excluded from the disinfection circulation. In other words, the disinfectant is passed merely into the one (discharge) side of the heat exchanger only at the end of the disinfection cycle, if at all, namely when the circulation valve is closed and the discharge valve is opened instead for disposing of the disinfectant. The opposite water intake side of the heat exchanger is not reached at all by the disinfectant. Moreover, the outflowing disinfectant passes the heat exchanger in a comparatively rapid manner and thus cannot have its full disinfecting effect.

In order to still bring about certain purification of the heat exchanger, the latter is flushed for several minutes on the water intake side by means of drawn water prior to treatment of a patient so as to effectuate at least certain reduction of germs. However, such reduction of germs achieved by mere flushing certainly does not correspond to an adequate disinfection so that there is still a residual risk of a contaminated dialysis fluid.

After expiry of the predetermined disinfection period furthermore the disinfectant has to be flushed as quickly as possible and the machine has to be cooled to approx. 35° C. again as quickly as possible so that the next treatment phase can be initiated. Since, however, the still hot disinfectant is passed through the heat exchanger on the discharge side thereof and simultaneously heats the inflowing water on the water intake side of the heat exchanger, consequently heated water is used for flushing the heat exchanger and for cooling the overheated fluid circulation, thereby the cooling of the machine being delayed.

Summing up, the problems occurring in the state of the art can be stated as follows:

The entrance area of the dialysis machine cannot be disinfected due to the design. Therefore, when designing a dialysis machine, this area is configured to have as small surfaces and short hose lengths as possible. Notwithstanding, each surface offers the possibility of microorganisms adsorbing and forming a so called biofilm. Consequently, a highly efficient heat exchanger would increase the contact surface many times over vis-à-vis a configuration comprising no heat exchanger. Therefore it would not be acceptable to leave such surface without disinfection.

It is a risk to connect the water intake line to the disinfection circulation due to the fact that in the case of low pressure in the water processing unit the water mixed with disinfectant enters into the external water circulation of the dialysis center and there it is harmful to the patients. In order to nevertheless realize such solution complex apparatuses would be required to safely prevent backflow into the water processing unit.

The dialysis fluid has to be heated by the inflow, for example at 10° C., to approx. 37° C. For a treatment about 120 l of fluid are required which results in a thermal energy requirement of approx. 3.6 kWh. Unless a heat exchanger is provided, such thermal output is generated electrically, whereby the power requirement of the dialysis machine is increased.

In the case of the dialysis machines according to the state of the art, usually a heat exchanger is employed which, however, has a comparatively small surface so as to cause less microbic contamination. Therefore, only a small fraction of the energy used can be re-used. Typical values for heat exchangers employed exhibit an efficiency of by far <50% so that, by calculation, there is still a minimum requirement of 1.8 kWh.

In the case of the existing heat exchangers delays occur upon cooling of the machine after disinfection cycles, because the heat exchanger is interconnected in the feed line even during the final flushing process. During the flushing phase at the end of disinfection, the machine is intended to reach a temperature of <40° C. again as quickly as possible so that the next treatment can be started as soon as possible. Hot disinfection is carried out at a temperature of >80° C., however. In the state of the art, during flushing the inflowing water would be heated by the permanently interconnected heat exchanger in an undesired way, thus the flushing phase and consequently the cooling phase being extended.

SUMMARY OF THE INVENTION

In view of the afore-discussed problems, it is an object of the present invention to provide a machine for extracorporeal blood treatment that reaches a higher degree of sterilization on the side of the (machine-side) fluid circulation. It is further a preferred target that the machine works more efficiently and more quickly. It is another preferred target to reduce the power consumption of the machine.

The afore-mentioned object and the further targets of the invention are achieved by a generic machine comprising the features of claim 1. Advantageous configurations of the invention are the subject matter of the subclaims.

Consequently, the core of the invention consists in arranging the circulation valve for changing over between the blood purification mode and the disinfection mode downstream of the heat exchanger. In this way, the heat exchanger is also interconnected in the disinfection circulation, whereby in the course of the disinfection cycle it is heated to almost the temperature of the disinfection fluid. This temperature is so high that germs can be destroyed both on the intake side (by the effect of the disinfectant itself) and on the discharge side of the heat exchanger (due to the high temperature).

Preferably a heat exchanger bypass line is provided which bridges the heat exchanger on the intake side during the disinfection cycle and/or during the flushing and cooling phase so that the heat exchanger does not heat the supplied purification cooling water for flushing the fluid circulation during/at the end of the disinfection cycle. In this way, the cooling of the fluid circulation can be accelerated at the end of the disinfection cycle.

It would be of advantage to use a heat exchanger having a heat transfer area of about 0.4 to 0.6 m² and preferably 0.5 m². Thus, on the one hand, good recovery of thermal energy is achieved in the blood purification mode and sufficient heating of the intake side of the heat exchanger is achieved in the disinfection mode for germ reduction.

It would also be advantageous when the heat exchanger forms a flow resistance that is higher than its bypass line. Thus it is unnecessary to connect a stop valve ahead of the heat exchanger so that the number of hydraulic elements to be switched can be kept small.

The following advantages over the state of the art can be achieved by the invention:
  The arrangement according to the invention permits adequate disinfection of the input side (intake side) of the heat exchanger due to heat by heat transfer from the output side (discharge side).
  The arrangement according to the invention permits adequate disinfection of the output side (discharge side) due to heat and disinfecting action of the disinfectant.
  The energy efficiency of the machine is increased, as a major part of the energy supplied during heating can be withdrawn from the discharged dialysis fluid. This is enabled by the use of highly efficient large-area heat exchangers without consideration of (no longer present) microbic contamination of the intake side.
  The new design of the fluid circulation according to the invention (including temperature switch) can be employed without modifications (of the machine control, for example) in each blood purification system of the relevant species.
  The machine consumes less energy and therefore is cost-effective and efficient compared to known solutions.

BRIEF DESCRIPTION OF THE DRAWINGS

The invention is best understood from the following detailed description when read in connection with the accompanying drawings. Included in the drawings are the following figures.

DETAILED DESCRIPTION OF THE EMBODIMENTS

Figure 1:
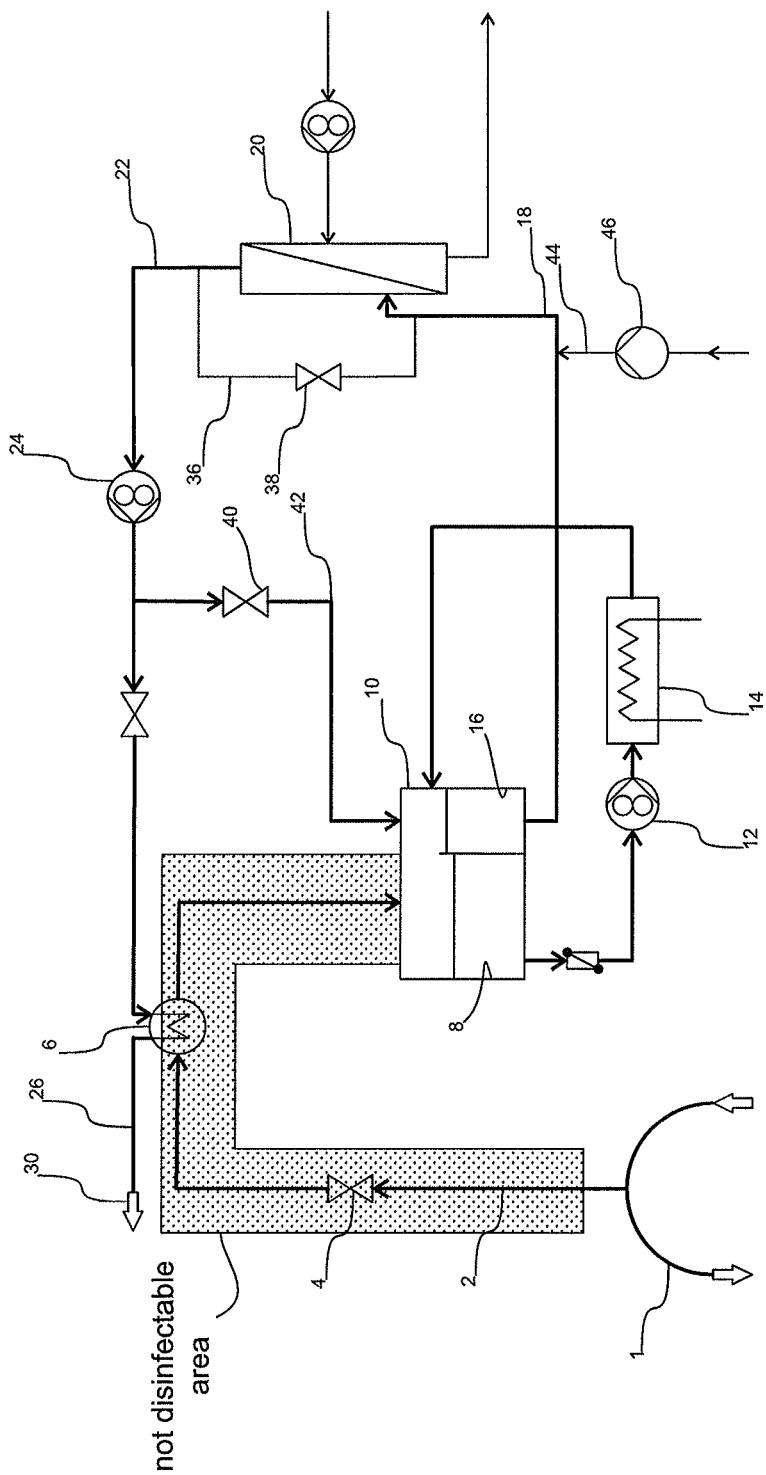
FIG. 1 shows the fluid circulation of a machine for extracorporeal blood treatment according to the state of the art.
Figure 2:
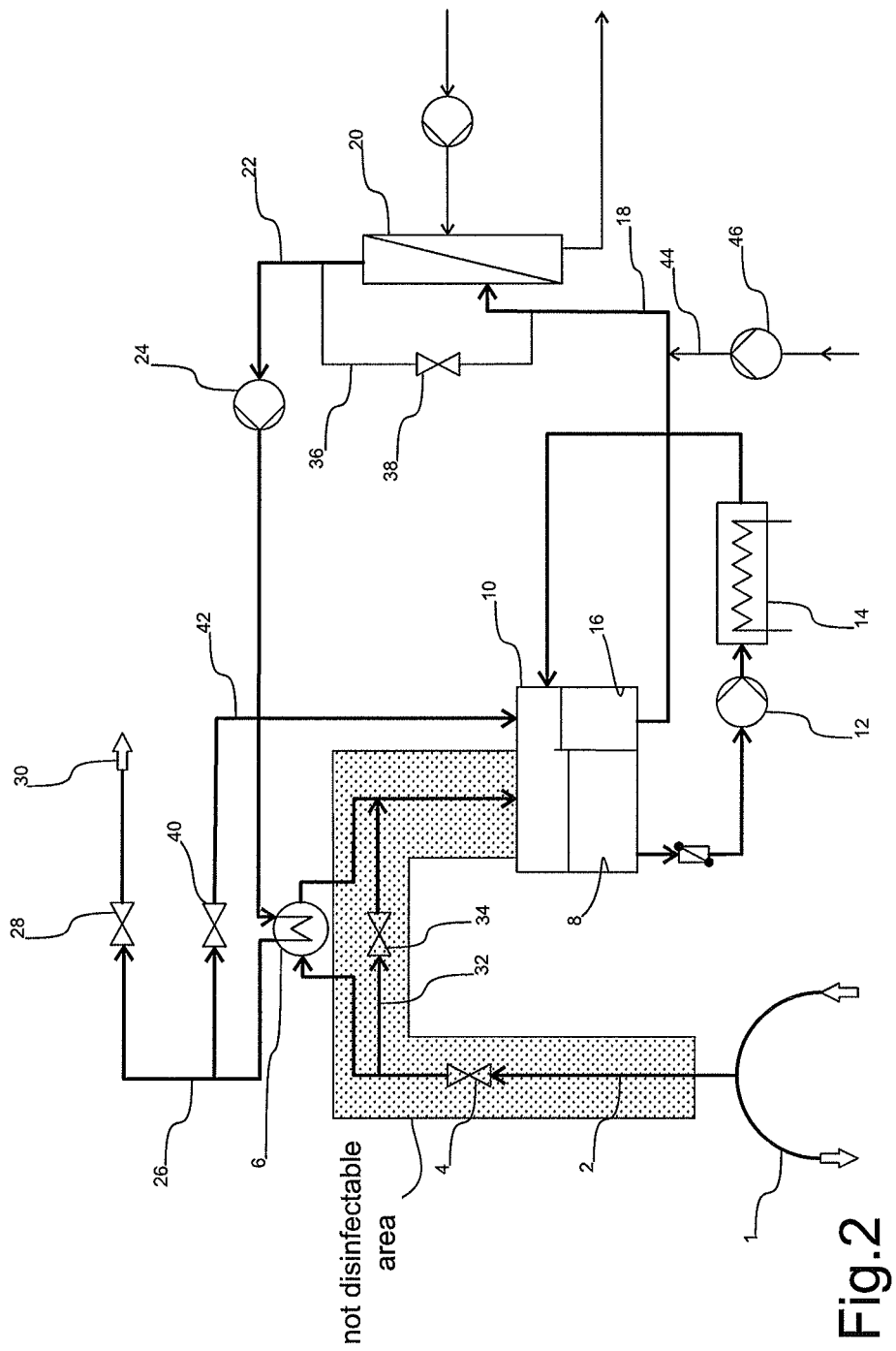
FIG. 2 shows the fluid circulation of a machine for extracorporeal blood treatment according to a preferred embodiment of the present invention.

The fluid circuit shown in FIG. 2 preferably is a purification fluid or dialysis fluid circulation of a blood purification or dialysis machine. However, it can also be a fluid circuit for other extracorporeal blood purification treatments such as the reduction of cholesterol in the blood or the like.

In the present embodiment of a dialysis machine, the machine-side fluid circuit (dialysis fluid circulation) is connected or connectable to a stationary osmosis or water ring main 1 of a dialysis center, wherein the water should be suited for dialysis treatment. Via a water feed line 2 in which an intake valve (stop valve) 4 is interconnected the water (suited for dialysis) is supplied to the intake side of the heat exchanger 6 for heating the latter, from where it is passed, in a now (pre-) heated state, into a first tank 8 of a water processing unit 10. From there the water is conveyed, while undergoing a degasification process, by a suction pump 12 into a heater 14 in which the water is heated to a temperature of about 37°, before it is then passed into a second tank 16 of the water processing unit 10. From here the intermediately stored water having a temperature of about 37° C. (and being suited for dialysis) is supplied, while a dialysis concentrate (not shown in detail) is added, thus now as a fresh/non-used dialysis fluid to a dialyser 20 via a first feed line 18 in order to absorb contaminants from a patient's blood via a dialyser membrane (not shown) according to a known dialysis treatment. The dialysis fluid, which afterwards is deemed to be used up, is then passed via a second feed line 22 including an interconnected flow pump 24 to the discharge side of the heat exchanger 6 in which it transfers its heat to the re-introduced water (e.g. osmosis water).

Finally the used and cooled dialysis fluid flows via a discharge line 26 and an interconnected discharge valve 28 into a drain 30 for disposal thereof.

As can further be inferred from FIG. 2, upstream of the intake valve 4 a bypass 32 branches off the intake line 2, the bypass connecting the input and the output of the intake side of the heat exchanger 6 and thus short-circuiting the heat exchanger 6 in a fluid-dynamic way. In the bypass 32 a heat exchanger bypass valve (stop valve) 34 is additionally interconnected. At the dialyser 20 a similar bypass 36 is provided which connects the first and second feed lines 18, 22 while short-circuiting the dialyser 20 and in which equally a dialyser bypass valve (stop valve) 38 is interconnected.

In parallel to the discharge valve 28 a circulation valve 40 is connected downstream of the discharge side of the heat exchanger 6. Concretely, a circulation line 42 in which the circulation valve (stop valve) 40 is interconnected and which opens into the water processing unit 10, preferably the first tank 8, branches off the discharge line 26 between the heat exchanger 6 and the discharge valve 28.

Finally, a disinfection line 44 is connected to the first feed line 18 between the dialyser 20 and the second tank 16 of the water processing unit 10, with a conveying pump 46 being interconnected in the disinfection line which conveying pump 46 in the operating state pumps disinfectant from a disinfectant reservoir not shown in detail into the first feed line 18 and in standstill (out of operation) blocks the disinfection line 44 in a fluid-tight manner.

The functioning of the blood purification machine according to FIG. 2 can be described as follows:
In blood purification mode (open fluid circuit) water is conveyed from the water or ring main 1 into the heat exchanger 6 and there is pre-heated. Then it flows into the first tank 8 of the water processing unit 10. Accordingly, the intake valve 4 is opened and the heat exchanger bypass valve 34 is closed.
After the water has passed the heater 14 (preferably an electric heating) and has been intermediately stored at a temperature of about 37° C. in the second tank 16 of the water processing unit 10, a dialysis concentrate is added to the water via a branch line not illustrated in detail, thereby the actual dialysis fluid being formed. The latter flows via the first feed line 18 into the dialyser 20 and from there is pumped, as used dialysis fluid, through the flow pump 24 in the second feed line 22 to the discharge side of the heat exchanger 6. After heat transfer to the re-conveyed fresh water the cooled used dialysis fluid flows into the drain 30 via the discharge valve 28. Hence, in this case the discharge valve 28 is opened, whereas the circulation valve 40 and the dialyser bypass valve 38 are closed.

In disinfection mode (closed fluid circuit) first the circulation valve 40, the heat exchanger bypass valve 34 and the dialyser bypass valve 38 are opened and the discharge valve 28 is closed. At the same time, the disinfection pump 46 is put into operation. Accordingly, fresh water flows into the water processing unit 10, while bypassing the heat exchanger 6, and from there into the heater 14 that heats the water to a temperature of approx. 85° C. or more. After repeatedly flowing through the water processing unit 10 (second tank 16), the hot water is mixed with disinfectant in the first feed line 18 and thus flows through the dialyser bypass line 36, the connected second feed line 22 and the discharge side of the heat exchanger 6. After that, the water-disinfectant mixture is returned via the circulation line 42 and the opened circulation valve 40 into the water processing unit 10, whereupon the afore-described circulation starts again.

Figure 3:
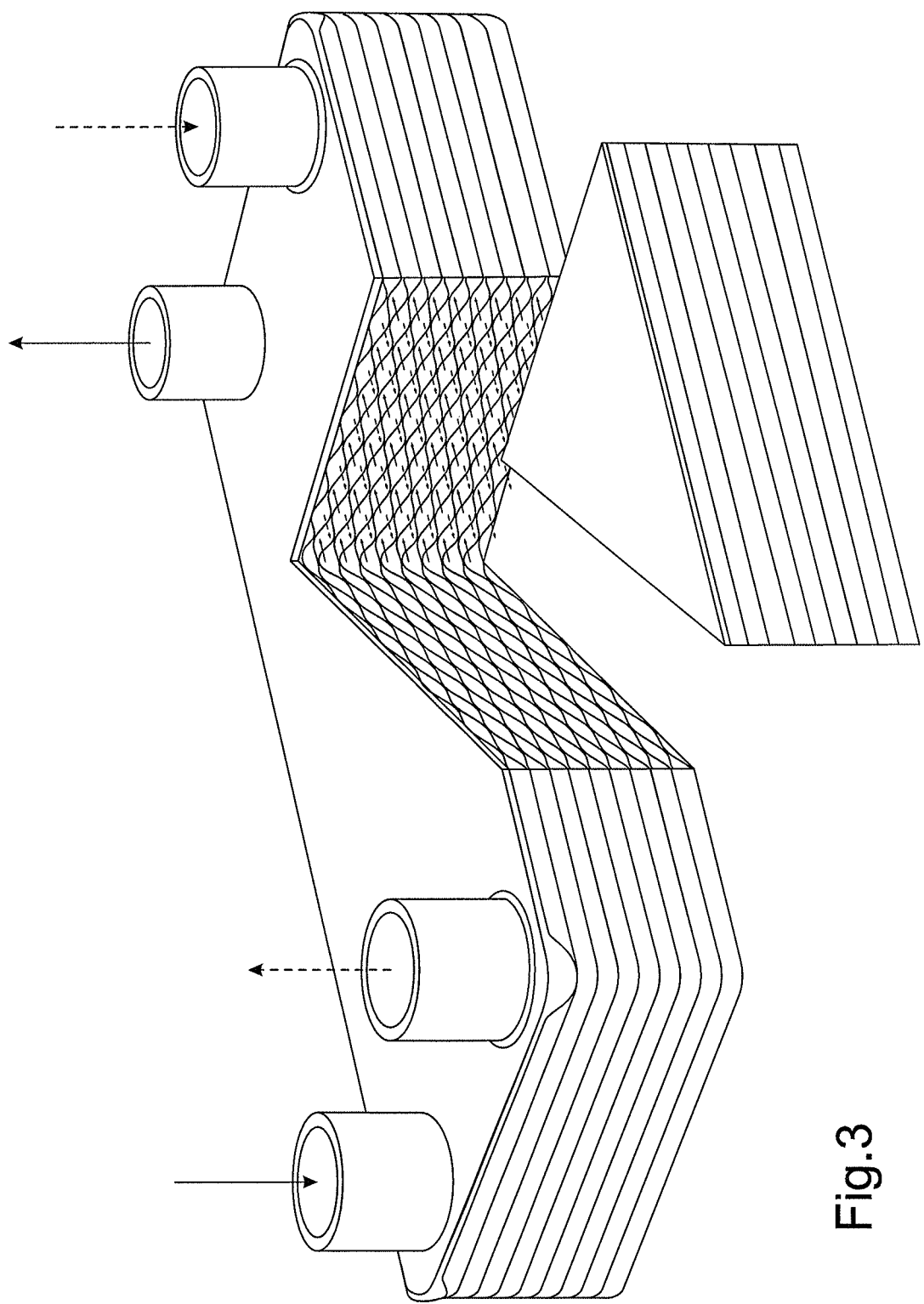
FIG. 3 shows the schematic representation of a heat exchanger as it is especially suited for the fluid circulation according to FIG. 2.

Since in the disinfection mode the intake side of the heat exchanger 6 is bridged, i.e. it is not constantly cooled by re-flowing water from the ring main 1, the heat exchanger 6 is (rapidly) heated on the whole by the hot disinfectant on its discharge side so that also its intake side is disinfected/sterilized due to the heat. This sterilizing effect is the greater, the larger the heat transfer area of the heat exchanger 6. It has turned out to be especially advantageous when the heat exchanger 6 according to FIG. 3 is interconnected in the fluid circuit preferably according to the counter flow principle. In accordance with the present preferred embodiment of the invention, the heat exchanger 6 is made of stainless steel and further preferably includes a heat exchange area of from 0.4 m$^2$ to 0.6 m$^2$, especially 0.5 m$^2$. Because of this large area and the counter flow principle provided in the heat exchanger 6, high efficiency of the heat transfer is ensured. This permits to obtain maximum energy recovery in the blood purification mode and, at the same time, to achieve optimum sterilization in the disinfection mode.

Toward the end of the disinfection mode, the disinfection pump 46 is switched off and the circulation valve 40 is closed. Subsequently, the discharge valve 28 is opened. In this switching position, fresh water is pumped through the fluid circuit while bypassing the heat exchanger 6 and the dialyser 22 in the open circulation without the heater 14 being actuated. That is, the fluid circuit is maximally cooled during this flushing process and is reset to the temperature optimal for the blood purification mode. After cooling the fluid circuit, the two bypass valves 34, 38 are closed and the heater 14 is set to 37° C.

As is evident from the foregoing functional description, the amount of inflowing fresh water and outflowing used dialysis fluid is substantially equal. When the afore-described highly efficient heat exchanger 6 is employed, the major part of the heat is transferred to the inflowing water. In the disinfection phase, in a first mode the heat exchanger bypass valve 34 can be switched by a temperature switch or, in a second mode, by way of software (by way of control) so as to guide the inflowing water past the heat exchanger 6. The temperature switch is preferably employed/arranged directly at the heat exchanger 6 or directly in the disinfection circulation.

The temperature switch can be designed so that the heat exchanger bypass valve 34 is safely closed in dialysis operation (e.g. <45° C.) and that the heat exchanger bypass valve 34 is safely open during disinfection and during flushing (e.g. >45° C.). The fresh water thus remains on the intake side of the heat exchanger 6 and is passively heated by conduction. This, in turn, results in a reduction of germs corresponding to adequate disinfection of $10^{-5}$. Moreover, the cooling phase of the machine is prevented from being extended, as the inflowing fresh water is not heated by the draining used fluid in the heat exchanger 6.

Summing up, a blood treatment machine or a machine for extracorporeal blood treatment is disclosed comprising a machine-side fluid circulation which, inter alia, comprises:

a heat exchanger for heating cold purification fluid freshly supplied on its intake side or water suited for blood purification, for which purpose used still warm purification fluid flows past its opposite discharge side for heat exchange and a circulation valve for changing over between a blood purification mode in which the used purification fluid is disposed of in an open fluid circuit through the discharge side of the heat exchanger and a disinfection mode in which hot disinfectant circulates in a closed fluid circuit. In accordance with the invention, the circulation valve is connected downstream of the heat exchanger with respect to the discharge side thereof.

The invention claimed is:

1. A machine for extracorporeal blood treatment comprising a machine-side fluid circulation, the machine comprising:
   a heat exchanger having an intake side and a discharge side, the heat exchanger configured to:
   receive fresh fluid at the intake side, the fresh fluid including dialysis fluid or water suitable for use in dialysis,
   heat the fresh fluid on the intake side,
   receive used dialysis fluid at the discharge side, the used dialysis fluid having retained heat, and
   transfer the retained heat of the used dialysis fluid in the discharge side to the fresh fluid in the intake side in a heat exchange;
   an intake valve configured to permit flow of the fresh fluid to the intake side of the heat exchanger in an open state during a blood purification mode, and not permit flow of the fresh fluid to the intake side of the heat exchanger in a closed state during a disinfection mode;
   a discharge valve configured to permit flow of the used dialysis fluid out of the discharge side of the heat exchanger for disposal in an open state during the blood purification mode, and not permit flow of the used dialysis fluid out of the discharge side in a closed state during the disinfection mode;
   a circulation valve connected downstream of the heat exchanger on the discharge side of the heat exchanger, the circulation valve configured to switch the machine between the blood purification mode and the disinfection mode,
   wherein the circulation valve is configured to be closed during the blood purification mode and open during the disinfection mode, wherein the blood purification mode is characterized by inflow of the fresh dialysis fluid or the fresh water into the intake side of the heat exchanger and by disposal of the used dialysis fluid through the discharge side of the heat exchanger in an open fluid circuit, and
   wherein the disinfection mode is characterized by circulation of a hot water-disinfectant mixture in a closed fluid circuit resulting from the closure of the intake valve and the closure of the discharge valve.

2. The machine according to claim 1, wherein the heat exchanger is included in the closed circuit during the disinfection mode.

3. The machine according to claim 1, further comprising a heat exchanger bypass line for at least partly bridging the intake side of the heat exchanger in the disinfection mode.

4. The machine according to claim 3, wherein in the bypass line further comprises an interconnected stop valve configured to selectively open the bypass line in the disinfection mode and to close it in the blood purification mode.

5. The machine according to claim 4, wherein the discharge valve connected to the discharge side of the heat exchanger is arranged in parallel to the circulation valve.

6. The machine according to claim 4, wherein the heat exchanger is made of non-corroding steel and includes a heat exchange area of from $0.4\ m^2$ to $0.6\ m^2$.

7. The machine according to claim 6, wherein the heat exchanger is operated on a counter flow principle.

8. The machine according to claim 6, wherein the heat exchanger forms a flow resistance higher than the flow resistance of the heat exchanger bypass when the stop valve is opened.

9. A method of using a heat exchanger in counter flow operation inside a machine according to claim 1, wherein the heat exchanger is made of non-corroding steel, and includes a heat exchange area of from $0.4\ m^2$ and $0.6\ m^2$; wherein the method comprises the steps of:

receiving, at an intake side of the heat exchanger, fresh fluid wherein the fresh fluid is dialysis fluid or water suitable for use in dialysis, heating, at the intake side of the heat exchanger, the fresh dialysis fluid or water, receiving, at a discharge side of the heat exchanger, used dialysis fluid having retained heat, and transferring, with the heat exchanger, the retained heat of the used dialysis fluid in the discharge side to the fresh fluid in the intake side in a heat exchange.

10. The method of using a heat exchanger according to claim 9, wherein the machine further comprises a heat exchanger bypass line configured to at least partly bridge the intake side of the heat exchanger in a disinfection mode and wherein the heat exchanger forms a flow resistance that is higher than the flow resistance of the heat exchanger bypass line including an opened stop valve arranged in the bypass line.

11. The machine according to claim 6, wherein the heat exchange area is about $0.5\ m^2$.

12. The method of using a heat exchanger according to claim 9, wherein the non-corroding steel is stainless steel.

13. The method of using a heat exchanger according to claim 9, wherein the heat exchange area is about $0.5\ m^2$.

* * * * *